United States Patent [19]

Lindh et al.

[11] Patent Number: 4,523,394
[45] Date of Patent: Jun. 18, 1985

[54] ANKLE LIGAMENT PROTECTIVE DEVICE

[76] Inventors: Kjell E. Lindh, Kardvägen 13, S-752 57 Uppsala; Kjell H. Sundin, Vårliden 6, S-791 32 Falun, both of Sweden

[21] Appl. No.: 394,925
[22] PCT Filed: Nov. 11, 1981
[86] PCT No.: PCT/SE81/00332
 § 371 Date: Jun. 30, 1982
 § 102(e) Date: Jun. 30, 1982
[87] PCT Pub. No.: WO82/01659
 PCT Pub. Date: May 27, 1982

[30] Foreign Application Priority Data

Nov. 12, 1980 [SE] Sweden ............... 8007953

[51] Int. Cl.³ ................... A43B 7/20
[52] U.S. Cl. .................. 36/89; 36/114; 128/166
[58] Field of Search ........ 36/89, 110, 114, 119, 36/88; 128/80 R, 83.5, 166; 2/22

[56] References Cited

U.S. PATENT DOCUMENTS 1,205,206 11/1916 Hofmeister ............... 36/89
3,383,708 5/1968 Pappas ...................... 2/22
3,506,000 4/1970 Baker ..................... 2/22 X
3,515,136 6/1970 Baker ..................... 2/22 X

FOREIGN PATENT DOCUMENTS 183418 4/1907 Fed. Rep. of Germany ...... 128/166

OTHER PUBLICATIONS

European Patent Application #5,615 to Rhee, Published Nov. 28, 1979, 37 pages Spec., 13 pages Drawings.

Primary Examiner—Henry S. Jaudon
Assistant Examiner—Tracy Graveline
Attorney, Agent, or Firm—Steele, Gould & Fried

[57] ABSTRACT

A foot ligament protective device comprising a foot plate (1), extending from the heel portion of the foot at least over the arch, an ankle sleeve (3) provided with fastening means (12, 13) and designed to be fixed around the ankle portion of the foot, and flexible but lengthwise substantially not extensible connecting members (2), which are arranged to connect the ankle sleeve (3) on both sides of the foot to the foot plate (1) in at least a fore and rear portion of the latter, such that sideways overstretching movements are prevented.

9 Claims, 5 Drawing Figures

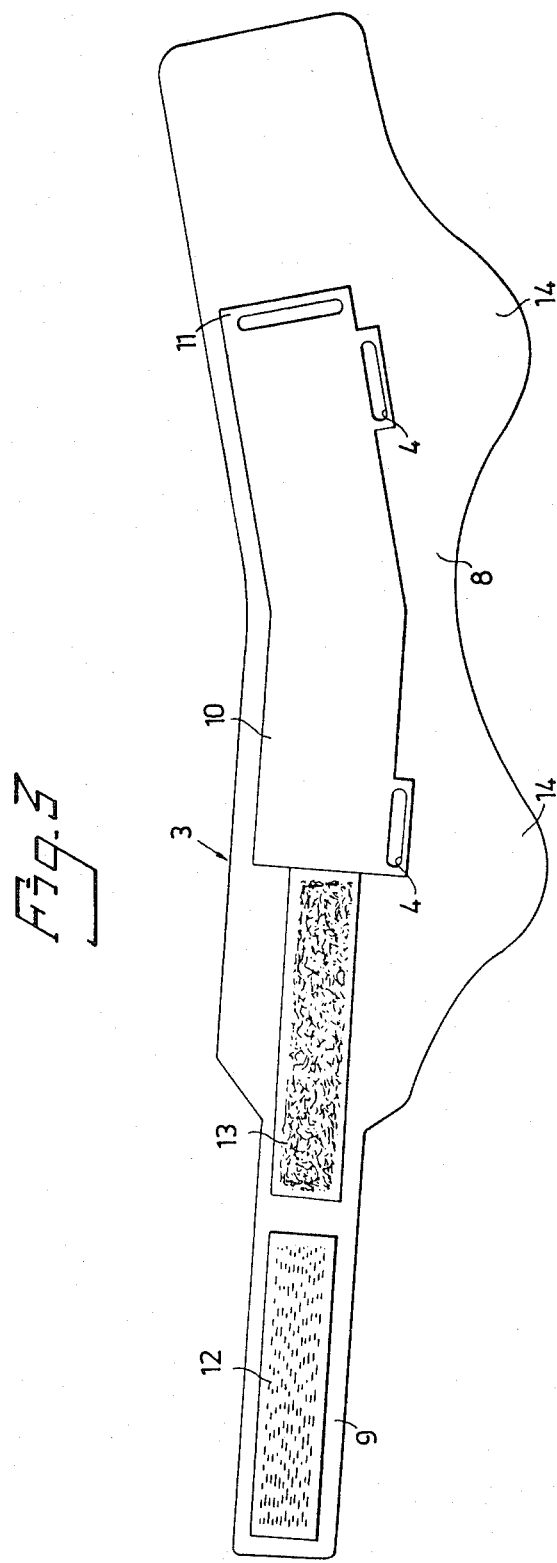

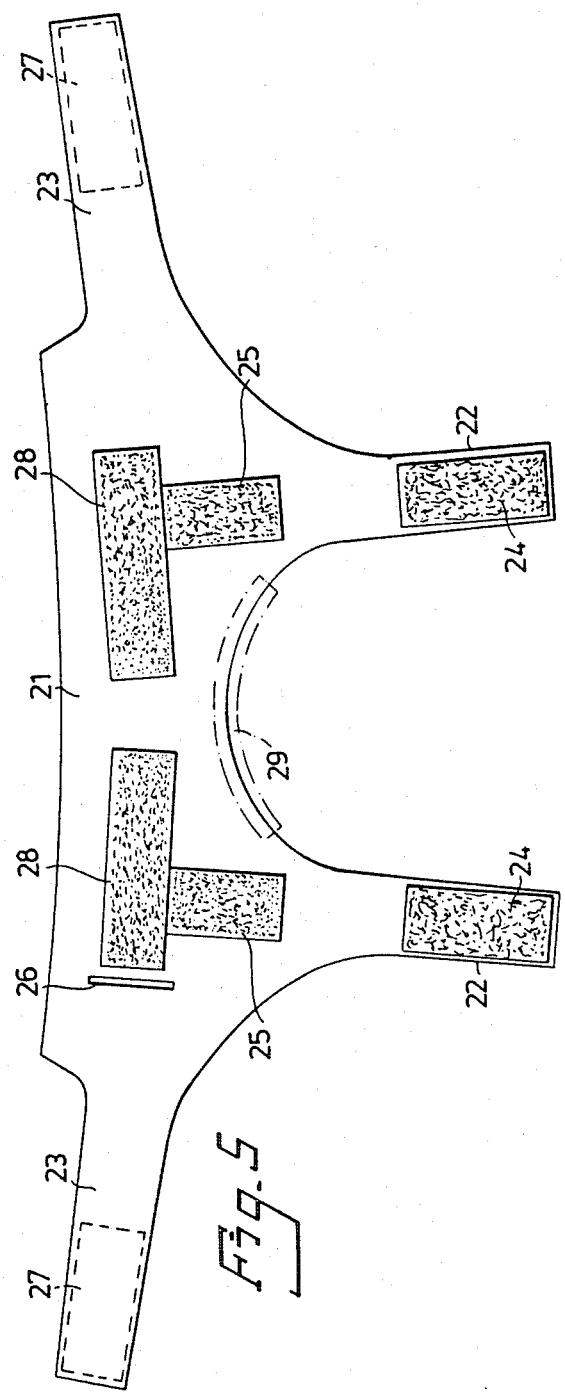
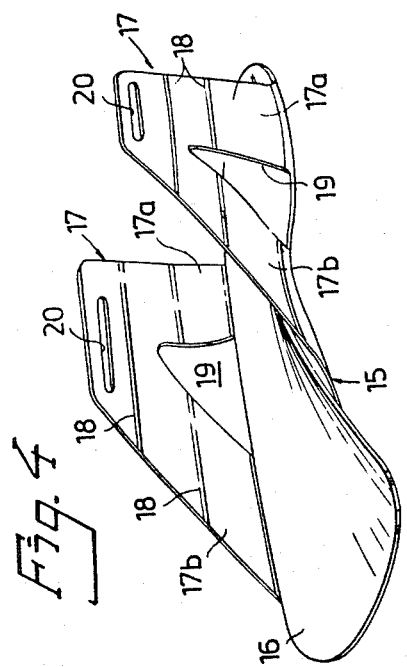

4,523,394

ANKLE LIGAMENT PROTECTIVE DEVICE

The present invention relates to a protective device for preventing ligament injuries of the ankle joints in connection with, for example, the practice of sports and athletics. The protective device is simple to apply and does not prevent the normal mobility of the foot.

Spraining injuries are responsible for a great part of the injuries in sports and athletics. Once sprained on some occasion, the ankle joint, as a rule, is permanently weakened, which makes it more susceptible to repeated injuries of the same kind. To prevent such injuries of a possibly weakened ankle joint, as well as to protect an injured joint in the healing process, so-called taping, i.e. wrapping of the ankle with a special tape, is often used. The tape is applied such that it functions as a support to the ankle joint but does not prevent the functions thereof. In addition to the fact that such a tape is relatively expensive, special knowledge and skill is required to apply an appropriate taping. Further, the supporting action of the tape is reduced if the tape becomes moist, e.g. by perspiration. For a good protective effect to be obtained in such a case, a new tape bandage must be applied. Thus, considerable amounts of money are spent on protective taping of the ankle joints ever year. In order to substantially eliminate the need for such taping, there is, according to the invention suggested a foot ligament protective device in the form of a support device for repeated use, which is simple to apply, which is flexible, which does not impede the mobility of the ankle, yet which prevents greater side stretching movements of the ankle joint than the ligaments and muscle tissue can stand.

SUMMARY OF THE INVENTION

According to a basic concept of the invention the foot ligament protective device comprises a relatively rigid foot plate or sole, which through connecting parts of a flexible but substantially not extensible material is connected to an ankle sleeve, designed to be firmly fixed around the ankle portion of the foot. The connecting parts connecting the ankle sleeve with the foot plate are arranged on each side of the foot and connected to the foot plate in at least a rear and a fore part of the latter, so that sideways overstretching of the ankle joint is prevented. These connecting parts are preferably designed in accordance with the anatomy of the foot, i.e. with the "tension directions" along the major ligaments of the foot and in directions towards the prominence of the ankle.

Preferably, the connecting parts or members are vertically adjustable to allow for anatomic differences between various individuals, and in a preferred embodiment the protective device of the invention comprises two separate parts removable from each other, viz. a foot plate part and an ankle sleeve part, which can be connected through suitable means. The connecting members may be arranged in various ways. Thus, they may, for example, be fixed to the foot plate and attachable to the ankle sleeve through suitable means. Alternatively, part of the connecting members may be fixed to or integral with the foot plate and part thereof fixed to or integral with the ankle sleeve, said connecting member parts being connectable to each other through suitable means. Further, the necessary flexibility of the connecting members may be achieved in various ways. For example, at least a major part of the connecting members may be made of a flexible, supple material, but they may also consist of a relatively stiff material provided with suitable links or link portions, such as thin material sections, indentations or the like. To provide the vertical adjustability and simple dismounting of the protective device, one of said connecting members and the ankle sleeve may comprise strap members and the other loop means, through which the straps are to be received, suitable fastening means being arranged for securing the straps in a desired position. Such fastening means, as well as the fastening means for fastening the ankle sleeve, may suitably comprise self-fastening material, e.g. the kind of tape sold under the trade name "Velcro" having hook and pile components.

Such a ligament protective device may easily be applied by the user and give excellent protection against sideways overstretching of the ankle joint (so-called spraining). In addition to the use in connection with sports, the ligament protective device of the invention may, of course, also be used in medical rehabilitation, etc. It should be noted, that although the protective device of the invention could be called a support, it is not a support in the conventional sense, since it does not actually support the ankle or restrict its normal mobility in any way, but only restricts too extensive sideways movements which would otherwise overstrain the ligaments and muscle tissue.

BRIEF DESCRIPTION OF THE INVENTION

The invention will hereinafter be described in more detail with regard to a particular embodiment thereof, to which it, however, is not restricted in any way. Reference is made to the accompanying drawings, wherein FIG. 1 is a oblique perspective front view of an embodiment of a foot ligament protective device according to the invention, FIG. 2 is an oblique perspective rear view of the foot ligament protective device of FIG. 1 having a schematically inserted phantom foot, FIG. 3 is a plan view of the outside of the ankle sleeve of the foot ligament protective device of FIGS. 1 and 2, FIG. 4 is an oblique perspective front view of a foot plate having connecting member parts integral therewith, and FIG. 5 is a plan view ot the outside of an ankle sleeve adapted to the foot plate of FIG. 4.

DETAILED DESCRIPTION OF THE PREFERRED EMBODIMENTS

Figure 1:
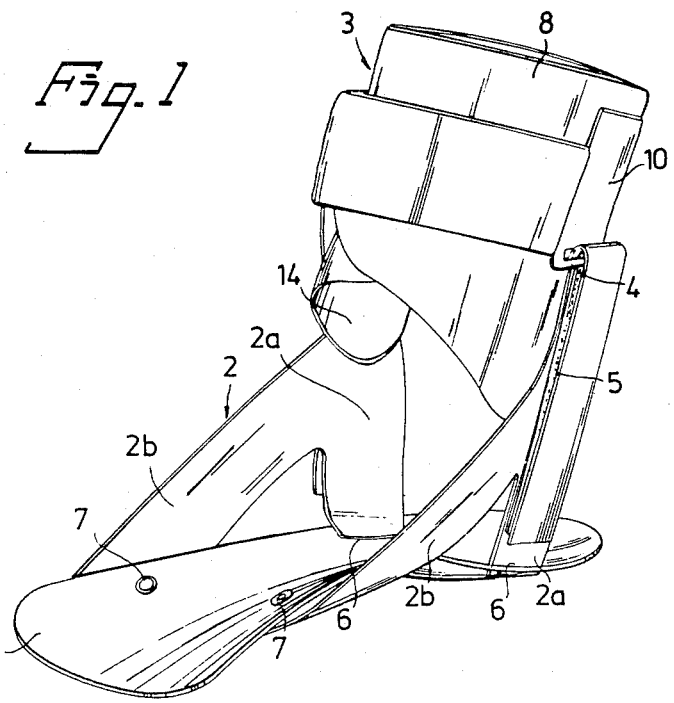
Figure 2:
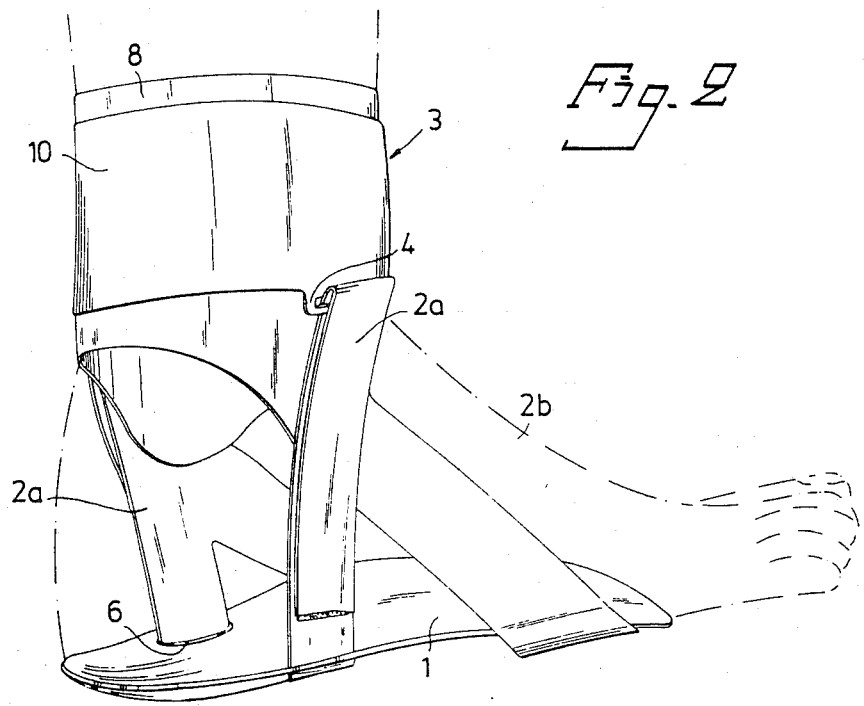

The ligament protective device of FIG. 1 comprises a foot plate or sole 1, which through connecting members 2 of a flexible material is connected to an ankle sleeve 3. The connecting members 2 should be substantially non-extensible in their longitudinal or connecting direction. The foot plate 1 is of a suitable, relatively rigid material, e.g. polyethene or similar plastic, and extends from the heel portion of the foot preferably up to, or almost up to, the first toe joint (FIG. 2). Suitably, the foot plate has a curved shape, which at least partially is adapted to the arch of the foot. As illustrated, the connecting members 2 consist of a band structure, which on each side of the foot plate 1 consists of a vertical band 2a attached to a rear part of the foot plate 1, and a band 2b extending obliquely downwards from the band 2a and attached to a fore part of the foot plate. At their upper parts the vertical bands 2a are drawn through loops 4 of the ankle sleeve 3 and arranged to be adjustable vertically in relation to the ankle sleeve, e.g. as in the figure by means of tape parts 5 of self-fastening material, such as "VELCRO" tape suitably arranged on the outside 2a of the bands, so that the upper parts of the bands can be folded back and fixed against the underlying parts in a desired position. The fastening of the bands 2a and 2b to the foot plate 1 may be performed in various ways. For example—as is intended in the Figure—the vertical bands 2a may be one single band going through slits 6 in the foot plate 1 and attached to the underside thereof, e.g. through glueing or riveting. The oblique bands 2b may be integral with the vertical bands 2a or be separate bands attached to the vertical bands in any suitable manner. The bands 2b are attached to a fore part of the underside of the foot plate 1, e.g. through glueing or with rivets. The directions of the bands 2a and 2b are arranged in accordance with the anatomy of the foot with substantially the same direction as the major ligaments of the foot and thus extending essentially towards the malleoli.

The construction of the ankle sleeve 3 is best shown in FIG. 3. The ankle sleeve comprises an elongate base portion 8, which on one side is extended with a tongue-like or strap part 9. The base part 8 is in the shown case provided with a reinforcement member 10, which has been fixed to the base part in a suitable manner, e.g. through glueing or welding. In the reinforcement member 10 said loops 4 are arranged. At the far end of the reinforcement member 10, as seen from the strap part 9, another loop 11 is arranged transversely to the loops 4. It can be seen from the phantom representation of the foot in FIG. 2 that the loops 4 are in substantial alignment with the prominences of the ankle, and therefore the axis of the ankle. The loop 11 is adapted to accommodate the strap part 9, so that the strap part can be passed through the loop, folded back towards the base part and fixed in a desired position by means of locking portions of self-fastening material, such as "VELCRO" tape, 12 and 13 attached to the strap part 9 and the base part 8, respectively, in any suitable manner. In the shown embodiment the base part 8 is provided with downwardly directed lug portions 14 which, when the foot ligament protective device is applied to the foot, extend downwards over the ankle prominences and prevent the upper portions of the bands 2a from chafing thereagainst.

The ankle sleeve should suitably have as large an area as possible without having a restricting effect on the mobility. The material should be tear resistent and substantially completely rigid in the connecting directions. However, some tensility in the transverse direction may be permitted. Further, it should give a good adhesion to the skin. A suitable material for the ankle sleeve 3 and the connecting bands 2 is a coated fabric, e.g. a synthetic fabric such as a polyester or a polyamide having a PVC-coating or the like, but other materials may, of course, also be used.

The bands connecting the ankle sleeve and foot plate are flexible, lengthwise adjustable but non-extensible connecting members. Lengthwise adjustment may be made by means of the "VELCRO" connection of the folded-over portion of connecting bands 2.

The foot ligament protective device of FIGS. 1 and 2 may easily be applied by the user. The foot is placed on the foot plate 1, the "VELCRO" tapes 5 are released and the ankle sleeve 3 is placed at a suitable level on the ankle. The ankle sleeve is then properly fastened in this position by drawing the strap portion 9 through the loop 11, tightening it and fixing the strap portion 11 against the base part 8 by means of the "VELCRO" tapes 12 and 13. Then the vertical bands 2a—and thereby also the inclined bands 2b—are fastened by means of the "Velcro" tapes 5. The applied foot ligament protective device is supple and may without any problems be used in the user's normal shoes, such as football shoes, running shoes, etc. The foot plate 1 will be fixed in position in the shoe, so that it substantially is kept immobile. The normal movements of the ankle will not be affected, whereas extreme sidestretching, which could injure ligaments and muscle tissue, is prevented by the vertical bands 2a and the inclined bands 2b, respectively. The former bands take up the stretching forces when the foot is strained sideways in its normal position, while the latter bands 2b take up the forces when the foot is strained in a more or less stretched position. In effect, the connecting members form a flexible swinging hinge having a single axis substantially coincident with the ankle, which permits foot movements throughout a normally full range of non-injurious positions, but prevents excessive sideways movements into positions likely to cause ligament injury.

An alternative embodiment of the foot ligament protective device is shown in FIG. 4 and FIG. 5, FIG. 4 showing the foot plate part and FIG. 5 showing the ankle sleeve part thereof. The foot plate 15 of FIG. 4 comprises a foot plate portion 16, corresponding to the foot plate 1 of FIGS. 1 and 2, which integral therewith has flexible connecting member parts 17 extending from both sides thereof. The connecting member parts 17 may possibly have a thinner material thickness than the actual foot plate 16, and to provide sufficient flexibility thereof, they are preferably provided with a sufficient number of weakening lines or indentations 18 (in the shown case three) extending substantially along the foot plate. The configuration of the connecting members 17 essentially corresponds to the lower part of the connecting members 2 of the embodiment shown in FIGS. 1 and 2. Thus, a vertical band section 17a corresponds to the vertical band 2a of FIGS. 1 and 2, and an inclined section 17b corresponds to the band 2b. The triangular recesses 19 separating said band-shaped sections 17a and 17b may possibly be omitted. At the top part of the connecting member parts 17 slits 20 are provided to receive corresponding strap members of the ankle sleeve of FIG. 5, as will be described below.

The ankle sleeve of FIG. 5, which is adapted to the foot plate member shown in FIG. 4, comprises a base portion 21 having a pair of substantially vertical strap members 22 and a pair of substantially horizontal strap members 23. The free ends of the strap members 22 are provided with self-fastening material means 24, such as "VELCRO" tape, adapted to interlock with corresponding means 25 on said base portion 21 when folded back against the latter. Each strap member 22 is designed to be threaded through the slits 20 of the foot plate side extensions 17, the loop formed between the base portion 21 and the strap member 22 then attaching the foot plate to the ankle sleeve when said self-fastening material means 24, 25 are interlocked.

The ankle sleeve of FIG. 5 also has different means for fastening it around the ankle than those of the sleeve in FIG. 3. At one end part of the base portion 21 a substantially vertical slit 26 is arranged, which is adapted to receive the free end of the strap member 23 at the other end of the base portion 21. Each strap member 23 is at the end parts thereof, on the side opposite to the one shown (i.e. facing the plane of the drawing), provided with self-fastening material means 27, similar to those of the strap members 22, which are indicated through broken lines. The fastening means 27 are capable of interlocking with corresponding fastening means 28 appropriately arranged along the base portion 21. Suitably an elongated pad-like member 29 is arranged at the lower edge of the base portion 21, as indicated through the broken lines.

When mounting the ankle support of FIGS. 4 and 5, the foot is placed on the foot plate 15, and the ankle sleeve is wrapped around the ankle with the opposite side to the one shown facing the ankle, i.e. with the fastening means 24, 25, 28 outwards. The ankle sleeve is then firmly fastened to the ankle by pulling the end of the right strap member 23 of FIG. 5 through the slit 26 and locking the fastening means 27 thereof against the left one of the corresponding fastening means 28 of the Figure. Simultaneously, or successively, the left strap member 23 is wrapped around the ankle in the opposite direction and applied against the fastening means 28 to the right in the Figure, so that its corresponding fastening means 27 interlocks therewith. Then, the ends of each vertical strap member 22 is threaded through the respective slit 20 of the foot plate 15, tightened properly, and folded back against the base portion 21 of the ankle sleeve, so that the respective complementary fastening means 24 and 25 interlock. The ankle support is now properly applied, and may easily be readjusted whenever necessary. The above mentioned pad-like member 29 is intended to protect the heal skin from a possible galling action of the corresponding edge of the ankle sleeve material. The above described embodiment has the same advantageous function and properties as those of the previously described embodiment of FIGS. 1 to 3. The strap/fastening means construction of FIG. 5 for securing the ankle sleeve to the ankle may, of course, also be applied to the embodiment of FIGS. 1 to 3, and vice versa.

The foot ligament protecting device according to the invention thus constitutes a light and supple support, which efficiently prevents spraining of the ankle. When necessary, the support can quickly and easily be refastened. As mentioned above, the protective device may be used for preventing purposes as well as during the healing process of an injury which has already occurred. With sportsmen and athletes, the support permits, for example, that the training after an injury can be started earlier.

The invention is, of couse, not restricted to the above particularly described and shown embodiment, but many variations and modifications are possible within the scope of the subsequent claims. Thus, the configuration of the connecting bands 2 and the ankle sleeve 3 may be designed in various ways. Other locking devices than the above "VELCRO" tapes may, of course, also be contemplated. Similarly, for example, the loops 4 and 11 may be metal loops. In this case rubber pads or the like are suitably provided on the inside of the ankle sleeve 3 as a protection particularly for the ankle prominences. In e.g. the embodiment shown in FIGS. 1 and 2 bands may possibly be provided which extend from the branch point between the bands 2a and 2b to the heel portion of the foot plate.

We claim:

1. An ankle ligament protective device adapted for use in an with a shoe, comprising:
   a foot plate adapted to be placed under a foot and extending from the heel portion to and under the arch of the foot, the shoe, when worn, forming means for securing the foot plate to the foot;
   an ankle sleeve having fastening means for attachment of the sleeve around and over the ankle portion of the lower leg, particularly above the prominence areas of the ankle; and,
   flexible, lengthwise non-extensible connecting members attaching the foot plate to the ankle sleeve, said members extending on each side of the ankle sleeve from a single point of attachment over a prominence area of the ankle to at least a rear part of the foot plate, the connecting members permitting foot movements through a normally full range of non-injurious positions, but preventing excessive sideways movements into positions likely to cause ligament injury, whereby said ankle ligament protective device can be worn with normal shoes which need not be specially adapted for use with said device.

2. A device according to claim 1, comprising a further flexible, lengthwise non-extensible member further connecting one of the prominence area portions of the ankle sleeve to at least a fore part of the foot plate.

3. A device according to claim 1, wherein the connecting members are lengthwise adjustable.

4. A device according to claim 1, wherein the connecting members are formed integrally with the foot plate.

5. A device according to claim 1, wherein the ankle sleeve is removable from the foot plate.

6. A device according to claim 1, wherein the connecting members comprise a first part integrally formed with the foot plate and a second part integrally formed with the ankle sleeve, and further comprising fastening means for connecting the first and second connecting parts to one another.

7. A device according to claim 1, wherein the connecting members are fixedly attached to the foot plate and releasably attachable to the ankle sleeve.

8. A device according to claim 1, wherein the connecting members are held in position by fastening means comprising hook and pile components.

9. A device according to claim 1, wherein the fastening means for the ankle sleeve comprises hook and pile components.

* * * * *